United States Patent [19]

Rosenbluth et al.

[11] Patent Number: 5,074,855
[45] Date of Patent: Dec. 24, 1991

[54] URINARY INCONTINENCE PAD

[75] Inventors: Robert F. Rosenbluth, Laguna Niguel; Jay A. Lenker, Laguna Beach; George R. Greene, Costa Mesa, all of Calif.

[73] Assignee: Advanced Surgical Intervention, Inc., San Clemente, Calif.

[21] Appl. No.: 639,921

[22] Filed: Jan. 10, 1991

[51] Int. Cl.$^5$ .................. A61F 5/44; A61F 13/15; A61F 13/20

[52] U.S. Cl. .................. 604/385.1; 604/329; 604/330; 604/347; 604/358

[58] Field of Search ............... 604/358, 360, 365, 369, 604/385.1, 386, 387, 389, 327, 331, 347, 352

[56] References Cited

U.S. PATENT DOCUMENTS

| | | | |
|---|---|---|---|
| 3,340,876 | 9/1967 | Hill | 128/295 |
| 3,512,185 | 11/1967 | Ellis | 4/110 |
| 3,661,155 | 5/1972 | Lindan | 128/295 |
| 3,857,394 | 12/1974 | Alemany | 604/385.1 |
| 3,983,873 | 10/1976 | Hirschman | 128/285 |
| 4,046,147 | 9/1977 | Berg | 604/385.1 |
| 4,198,979 | 4/1980 | Cooney et al. | 128/295 |
| 4,209,009 | 6/1980 | Hennig | 604/385.2 |
| 4,421,511 | 12/1983 | Steer et al. | 604/329 |
| 4,457,314 | 7/1984 | Knowles | 128/760 |
| 4,484,917 | 11/1984 | Blackmon | 604/327 |
| 4,496,355 | 1/1985 | Hall et al. | 604/327 |
| 4,563,183 | 1/1986 | Barrodale et al. | 604/329 |
| 4,593,053 | 6/1986 | Jenne et al. | 523/111 |
| 4,595,392 | 6/1986 | Johnson et al. | 604/385 |
| 4,627,848 | 12/1986 | Lassen et al. | 604/370 |
| 4,673,403 | 6/1987 | Lassen et al. | 604/385.1 |
| 4,673,403 | 6/1987 | Lassen et al. | 604/385 |
| 4,690,677 | 9/1987 | Erb | 604/329 |
| 4,804,380 | 2/1989 | Lassen et al. | 604/385 |
| 4,822,347 | 4/1989 | MacDougall | 604/329 |
| 4,846,819 | 7/1989 | Welch | 604/329 |
| 4,846,824 | 7/1989 | Lassen et al. | 604/385 |
| 4,979,947 | 12/1990 | Berman | 604/369 |
| 4,990,338 | 2/1991 | Blank et al. | 604/358 |

FOREIGN PATENT DOCUMENTS 754481 8/1956 United Kingdom ................ 81/2

Primary Examiner—David J. Isabella
Assistant Examiner—Elizabeth M. Burke
Attorney, Agent, or Firm—Klein & Szekeres

[57] ABSTRACT

A device for controlling urinary incontinence in a human female, comprising a resilient pad, configured to seal against and occlude the urethral meatus of the user. The pad includes a base that is adapted to seat against the vestibule of the user's vulva, anteriorly of the vaginal orifice, thereby covering the urethral meatus. An adhesive is provided on the base to seal against and occlude the urethral meatus, and to retain the pad in place against the vestibule. The pad has lateral edges that fit inside the labia minora of the user, to aid in retention of the device. The surface of the pad opposite the base is formed into a longitudinal stiffening ridge that extends into the interlabial space. A handle is attached to the ridge to facilitate removal.

31 Claims, 1 Drawing Sheet

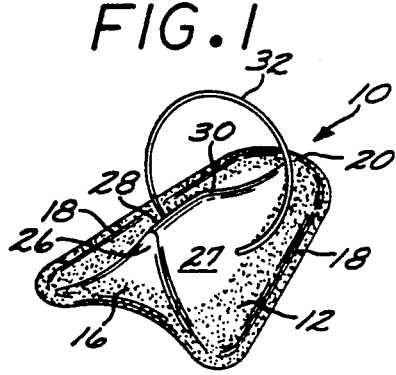
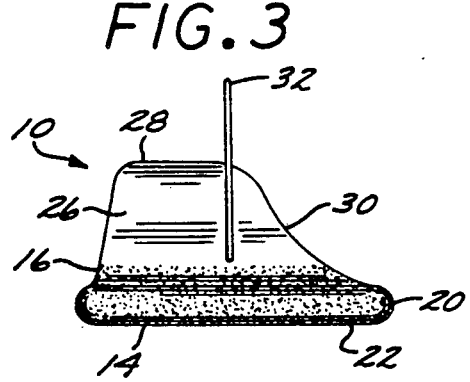
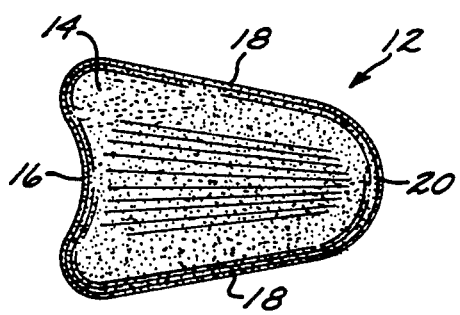
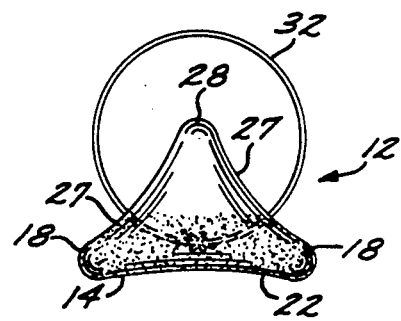
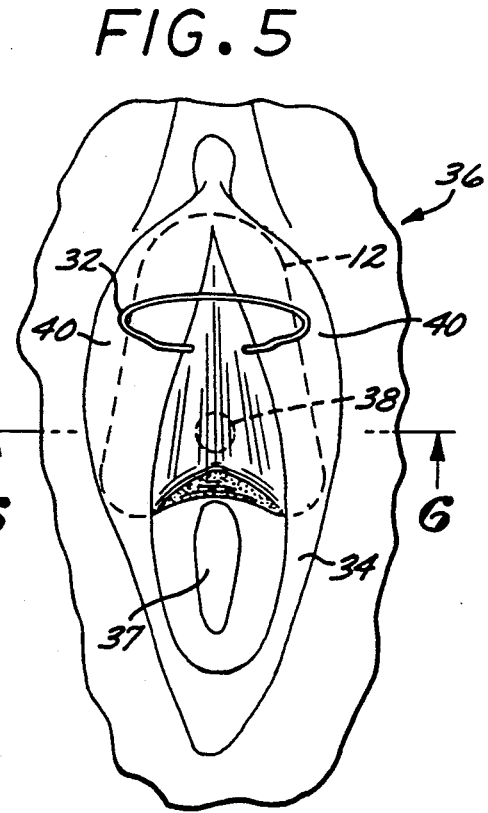
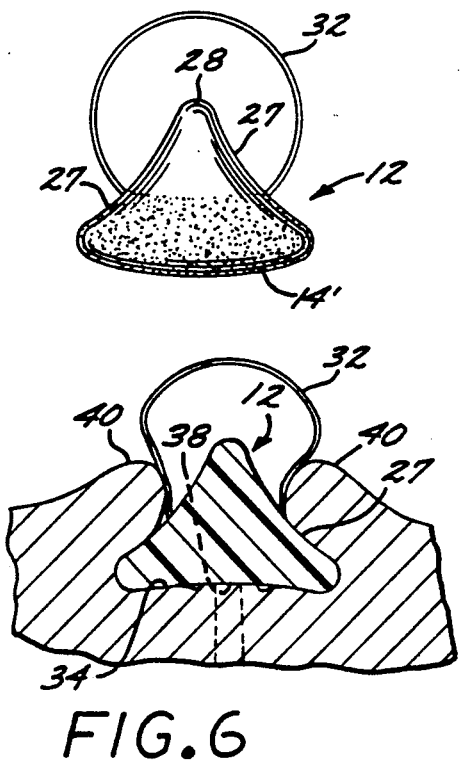

URINARY INCONTINENCE PAD

BACKGROUND OF THE INVENTION

This invention relates to the field of devices or appliances used to relieve or mitigate the problems associated with human urinary incontinence. More specifically, the present invention relates to a removable external closure for the human female urethra.

Urinary incontinence, due to disease, injury, or other causes, is a troublesome problem for many individuals. Surgical intervention is often required to treat severe cases of incontinence, but in those cases where the patient suffers from only a partial loss of bladder control, or where the patient is a poor candidate for surgery or does not desire to undergo surgery, nonsurgical treatment is called for. Such nonsurgical approaches are particularly appropriate for female patients who suffer from the partial, sporadic loss of bladder control sometimes referred to as "stress incontinence" or "urge incontinence". Such stress or urge incontinence, in fact, is the most common cause of involuntary urine loss in adult women.

Nonsurgical management of female urinary incontinence includes non-therapeutic management, wherein the patient wears an appliance or device proximate the urethral orifice ("meatus") that collects or captures urinary discharge. Such devices fall generally into two categories: (1) urine collection devices, and (2) absorbent pads.

Urine collection devices typically comprise a receiving orifice or receptacle for capturing urine flowing from the urethra; retention means, associated with the receptacle or orifice, for holding the receptacle or orifice in the proximity of the urethral meatus; and means for directing urine from the receptacle or orifice to a reservoir or a container or the like for disposal. Devices of this general description are disclosed in the following U.S. Pat. Nos.: 3,512,185—Ellis; 3,661,155—Lindan; 4,412,511—Steer et al.; 4,457,314—Knowles; 4,484,917—Blackmon; 4,690,677—Erb; 4,822,347—MacDougall; and 4,846,819—Welch. A variation on the urinary collection device theme is the "female external catheter", disclosed in U.S. Pat. No. 4,563,183—Barrodale et al., which includes a catheter tube having one end inserted into the urethra. In many of these devices, the retention means are configured so as to be inserted into the interlabial space, being retained therein by the anatomical structure of the external female genitalia. The Blackmon and MacDougall devices also use an adhesive to assist in retention.

The category of absorbent pads includes a wide variety of devices which generally comprise a body of absorbent material configured so as to be insertable into the interlabial space, and retained therein by the anatomical structure of the external female genitalia. Such devices typically resemble (and, indeed, can function as) catamenial sanitary napkins. The following U.S. Patents disclose devices that may generally be considered within this category: U.S. Pat. Nos. 3,983,873—Hirschman; 4,595,392—Johnson et al.; 4,627,848—Lassen et al.; 4,673,403—Lassen et al.; 4,743,245—Lassen et al.; 4,804,380—Lassen et al.; and 4,846,824—Lassen et al. A sanitary napkin that is configured for interlabial retention, and that could be used to capture and absorb urine flow, is disclosed in British Patent No. 754,481.

While the above-described devices are useful in certain applications, they are subject to a number of disadvantages. For example, the urine collection devices require the user to wear a reservoir or container that may be prone to overflow or spillage Also, such devices are better suited to users who suffer from chronic or severe loss of bladder function, rather than those who suffer only from stress or urge incontinence. The absorbent pads tend to be bulky, and may be uncomfortable for some users, especially when wet.

Use of the prior art devices described above is based upon the assumption that the flow of urine out of the urethra cannot or should not be stopped. This assumption may not be true in many cases of stress or urge incontinence. In such cases, external occlusion of the urethral meatus may provide an adequate degree of continence for many patients, but this approach has been overlooked by the prior art.

There is, therefore, a need for a device that provides for the effective management of female stress or urge incontinence by means of the external occlusion of the urethral meatus; that is easy to use and comfortable to wear; and that provides for secure retention with good sealing qualities.

SUMMARY OF THE INVENTION

Broadly, the present invention is a urethral meatus occlusion device, comprising a pad configured to engage and seal against the urethral meatus, and to be retained in place by adhesion to at least a part of the anatomical structure of the external female genitalia, which includes the vestibule, the meatus, and the labia minora. More specifically, the pad includes a base, having a substantially triangular or arrowhead-shaped outline, that is adapted to seat against the vestibule of the vulva, anteriorly of the vaginal orifice, thereby occluding the urethral meatus. The lateral edges of the pad are configured to fit inside the labia minora. The adhesive engagement between the pad and the vestibule thereby retains the pad firmly against the vestibule, in sealing engagement against the meatus. The engagement between the lateral edges and the labia minora enhances the retention of the pad. The side of the pad opposite the base is configured with a central longitudinal stiffening ridge that, when the pad is installed in the vestibule, extends into the interlabial space. A handle or tab is provided to facilitate removal of the device.

In a preferred embodiment of the invention, the base of the pad is coated with a pressure sensitive, hydrophilic hydrogel adhesive, for retention, against the vestibule. The adhesive, in concert with the resilient pad, spreads to fill the interlabial space proximate the vestibule, thereby providing a conformal fit with the anatomical structure which enhances the retention of the device. The pad itself can be coated or impregnated with a suitable anti-bacterial or germicidal agent, or such an agent can be included in this adhesive.

It will be appreciated that the present invention offers a new and advantageous approach to the management of stress and urge incontinence. For example, the device is small, unobtrusive, easy to use, and comfortable to wear. By allowing the user effectively to retain urine, the device avoids the problems associated with prior art devices, enumerated above, that allow the discharge of urine. The device can be made in a variety of sizes and shapes for optimal fit for each individual user. The device is economical to manufacture, and can, therefore, be a disposable item.

These and other advantages will be better appreciated from the detailed description that follows.

BRIEF DESCRIPTION OF THE DRAWINGS

FIG. 1 is a perspective view of a female urinary incontinence device, in accordance with a preferred embodiment of the invention;

FIG. 2 is a bottom plan view of the device of FIG. 1;

FIG. 3 is a side elevational view of the device of FIG. 1;

FIG. 4 is an anterior elevational view of the device of FIG. 1;

FIG. 5 is plan view of the device of FIG. 1, showing the device installed in the external genitalia of a human female;

FIG. 6 is a cross-sectional view taken along line 6—6 of FIG. 5; and

FIG. 7 is an anterior elevational view of an alternative embodiment of the device.

DETAILED DESCRIPTION OF THE INVENTION

Referring first to FIGS. 1 through 4 of the drawings, a female urinary incontinence device 10, in accordance with a preferred embodiment of the present invention, is shown. The device comprises a body or pad 12, formed of a resilient material that is biocompatible. One suitable class of materials is that of foams formed from the water actuation of prepolymers based on either toluene diisocyanate (TDI) or methylene diphenyl diisocyanate (MDI). Such prepolymers are marketed by W. R. Grace & Co.-Conn., Organic Chemicals Division, Lexington, Mass., under the trademarks "HYPOL" (TDI) and "HYPOL PLUS" (MDI).

The pad 12 includes a base 14 that has the general outline of a blunt arrowhead, as shown in FIG. 2. In the preferred embodiment of the invention, the base is slightly concave, as shown in FIG. 4. Alternatively, a base 14' can be provided that is slightly convex, as shown in FIG. 7, for those users who might find such a configuration more comfortable to wear. The pad 12 has a concave posterior end 16, with lateral edges 18 that taper slightly toward each other as they extend toward a rounded anterior end 20. The anterior end 20 is thus somewhat narrower than the posterior end 16.

The pad is provided with an adhesive surface for retention against the vestibule. In the preferred embodiment of the invention, the base is coated with an adhesive layer 22, comprising a pressure-sensitive, hydrophilic hydrogel adhesive material. Such hydrogel adhesives are marketed by Promeon Division of Medtronic, Inc., of Minneapolis, Minn., under the trademark "PROMEON". A detailed description of such a hydrogel composition is contained in U.S. Pat. No. 4,593,053—Jevne et al., the disclosure of which is incorporated herein by reference.

Alternatively, the material of the pad itself can be rendered adhesive by combining the TDI or MDI one to one by weight with about 0.25 to 0.50 molar ammonium hydroxide during the water-actuation of the foam. The resulting material has a surface that is positively charged, so that it will adhere to a negatively-charged mucoid surface (such as the vestibule and the inner portions of the labia minora).

The side of the pad 12 opposite the base 14 includes a central longitudinal stiffening ridge 26 which forms the thickest part of the pad 12. If one adopts the convention that the base is the "bottom" of the pad 12, then the pad can be defined as having a surface 27 opposite the base that slopes "downwardly" from either side of the ridge 26 toward the edges 18, so that there is a gradual reduction in pad thickness from the ridge to the edges. Viewed another way, the pad can be defined as having a three-dimensional form with a cross-sectional shape that narrows from the base 14 to the "top" or apex 28 of the ridge 26. The resulting configuration is such that a lateral cross section of the pad, taken through the ridge 26, produces a shape resembling a triangle with rounded corners and slightly concave sides, as shown in FIG. 6. Similarly, the ridge 26 has an anterior edge 30 that tapers "downwardly" from the apex 28 toward anterior end 20 of the pad 12, as shown in FIG. 3, so that the anterior end 20 of the pad 12 is substantially reduced in thickness as compared to the posterior end 16.

The device 10 is advantageously provided with a handle or tab that is either integrally molded with the pad, or subsequently attached to it. In the preferred embodiment, the handle is a ring or loop 32, preferably of thread, that is inserted laterally through the pad 12. The loop is preferably located near the anterior edge 28 of the ridge 26, although the precise location of the loop 32 is not critical to its function, as will be described below.

FIGS. 5 and 6 show the incontinence device 10 installed in the external genitalia of a human female. The device 10 is installed so that the base 14 is seated against the vestibule 34 of the vulva 36, anteriorly of the vaginal orifice 37, thereby occluding the urethral meatus 38. The adhesive surface seals the meatus sufficiently to prevent the escape of urine. The lateral edges 18 and the anterior end 20 of the pad are tucked under the labia minora 40. The engagement between the labia minora and the sloping surface 27 enhances the retention of the pad 12 in engagement with the vestibule 34. The concavity in the posterior end 16 of the pad 12 allows for somewhat greater surface area for engagement by the labia minora, while leaving a clearance for the vaginal opening 37. The ridge 26 extends into the interlabial space, and the loop 32 protrudes from between the labia majora (not shown), so as to be exposed to facilitate manual grasping, for removal of the device.

The pad 12 can be provided in a number of sizes to fit a large variety of individuals. The length of the pad should be approximately the same as the distance between the anterior lip of the vaginal orifice and the juncture of the labia minora. The width of the pad should optimally conform substantially to the width of the vestibule. Predetermined sizes can be trimmed individually for optimum fit. In some cases, a mold of the relevant portions of the vulva may be taken prior to sizing the pad.

The adhesive layer 22 not only provides a fluid-tight seal for the urethral meatus, but it also minimizes slippage of the device. The central ridge 26 lends rigidity that resists deformation of the pad and rupture of the adhesive layer under fluid pressure from the urethra, thereby enhancing the fluid-tight seal provided by the pad against the urethral meatus. It may be advantageous to extend the adhesive layer onto the labia-engaging surface 27, thereby further enhancing the stability of the device.

An incontinence device constructed in accordance with the preferred embodiment of the invention, as described above, can be made to withstand fluid pressures from the urethra in the range of up to at least about 100, and preferably to about 170 centimeters of water without significant leakage. Pressures in this range are in excess of those that would typically result in involuntary urine voiding in cases of stress and urge incontinence, with 170 centimeters of water being the approximate maximum bear-down pressure for a typical adult human female.

As an option, the foam material of the pad, and/or the adhesive surface, can be provided with a medically-active composition. An antibacterial or germicidal agent, such as silver oxide or silver azide may be used, for example.

From the foregoing, the advantages of the present invention will be readily appreciated. The incontinence device in accordance with the present invention provides effective management of female urinary incontinence, especially stress and urge incontinence, without the inconvenience and discomfort associated with prior art urine collection devices and absorbent pads. The present invention is easy to use and comfortable to wear. It is easily shaped and sized to fit each individual user's anatomy with optimum effectiveness and comfort. Easily and inexpensively manufactured, the present invention can be made as a disposable item. It is advantageously sold sterile, and packaged in a compact case (not shown) that holds several devices and fits in a purse or pocket. The case may include a mirror and/or a light to facilitate insertion.

While a preferred embodiment has been described above, it should be understood that a number of modifications and variations will suggest themselves to those skilled in the pertinent arts. Such variations and modifications should be considered within the spirit and scope of the invention, as defined in the claims that follow.

What is claimed is:

1. An incontinence device for controlling urinary incontinence in a human female, comprising:
   a pad having a shape and sized for fitting between the labia minora and the vestibule and including a base and adhesive means on said base for sealing against and occluding the urethral meatus of the user, the pad being retained in place against the urethral meatus substantially by adhesion to the vestibule of the user.

2. The device of claim 1, wherein the pad comprises:
   a base that seats against the vestibule of the vulva of the user; and
   adhesive means on the base, for sealing against and occluding the urethral meatus.

3. The device of claim 1, wherein the pad is made of a biocompatible foam material.

4. The device of claim 3, wherein the foam material is formed from the water actuation of a prepolymer selected from the group consisting of toluene diisocyanate and methylene diphenyl diisocyanate.

5. The device of claim 2, wherein the adhesive means includes a pressure-sensitive hydrophylic hydrogel material applied to the base.

6. The device of claim 2, wherein the pad is made of a foam material formed from the water actuation of a prepolymer selected from the group consisting of toluene diisocyanate and methylene diphenyl diisocyanate, and wherein the adhesive means is formed by reacting the prepolymer with ammonium hydroxide during the water actuation thereof.

7. The device of claim 1, further comprising:
   handle means, operatively connected to the pad, for facilitating the removal of the device from the user's external genitalia.

8. The device of claim 2, wherein the pad includes a posterior end, an anterior end, and a pair of lateral edges converging toward the anterior end, and wherein the base is dimensioned to seat against the vestibule anteriorly of the vaginal orifice of the user, inside the labia minora of the user, whereby the engagement between the labia minora and the pad contributes to the retention of the base against the vestibule.

9. The device of claim 8, wherein the pad includes a side opposite the base, the opposite side having a longitudinal ridge that extends into the interlabial space of the user.

10. The device of claim 9, wherein the ridge has a longitudinal apex, and wherein the pad is shaped such that a lateral cross-section through the ridge narrows from the base to the apex.

11. The device of claim 10, wherein the pad is shaped such that a lateral cross-section through the ridge has a substantially triangular shape with rounded corners and slightly concave sides.

12. The device of claim 11, wherein the ridge has a tapered anterior edge, whereby the anterior end of the pad is substantially reduced in thickness as compared to the posterior end.

13. The device of claim 9, further comprising a handle extending from the ridge, whereby the handle extends between the labia majora of the user when the base of the pad is seated against the vestibule.

14. An incontinence device for controlling urinary incontinence in a human female user, comprising;
   a pad having a base that seats against the vestibule of the vulva of the user, so as to cover that portion of the vestibule anterior of the vaginal opening of the user, the pad having an anterior end, a posterior end, and a pair of lateral edges converging from the posterior end to the anterior end, the lateral edges and the anterior end of the pad fitting under the labia minora of the user; and
   adhesive means on the base for providing a fluid-tight seal against the urethral meatus of the user;
   whereby the seating engagement of the base against the vestibule is substantially maintained by the adhesive engagement between the vestibule and the pad.

15. The device of claim 14, further comprising a handle attached to the pad so as to extend between the labia majora of the user when the base is seated against the vestibule.

16. The device of claim 14, wherein the pad is formed of a resilient foam material.

17. The device of claim 16, wherein the foam material is formed from the water actuation of a prepolymer selected from the group consisting of toluene diisocyanate and methylene diphenyl diisocyanate.

18. The device of claim 14, wherein the pad includes a medically-active composition.

19. The device of claim 14, wherein the pad includes a side opposite the base, the opposite side having a longitudinal ridge that extends into the interlabial space of the user.

20. The device of claim 19, wherein the ridge has a longitudinal apex, and wherein the pad is shaped such that a lateral cross-section through the ridge narrows from the base to the apex.

21. The device of claim 20, wherein the pad is shaped such that a lateral cross-section through the ridge has a substantially triangular shape with rounded corners and slightly concave sides.

22. The device of claim 21, wherein the ridge has a tapered anterior edge, whereby the anterior end of the pad is substantially reduced in thickness as compared to the posterior end.

23. The device of claim 14, wherin the adhesive means includes a hydrogel adhesive applied at least to the base of the pad.

24. The device of claim 17, wherein the adhesive means is provided by reacting the prepolymer with ammonium hydroxide during the water actuation thereof.

25. An incontinence device for controlling incontinence in a human female user, comprising;
 a pad having a base that seats against the vestibule of the vulva of the user, so as to cover that portion of the vestibule anterior of the vaginal opening of the user, the pad having an anterior end, a posterior end, and a pair of lateral edges converging from the posterior end to the anterior end, the lateral edges and the anterior end of the pad fitting under the labia minora of the user;
 a surface on the pad opposite the base, the surface forming a longitudinal ridge that extends into the interlabial space of the user when the base is seated against the vestibule;
 adhesive means on the base for providing a fluid-tight seal against the urethral meatus of the user; and
 handle means, attached to the ridge so as to extend between the labia majora of the user when the base is seated against the vestibule, for facilitating removal of the device by the user.

26. The device of claim 25, wherein the pad is made from a foam material formed from the water actuation of a prepolymer selected from the group consisting of toluene diisocyanate and methylene diphenyl diisocyanate.

27. The device of claim 25, wherein the adhesive means comprises a hydrogel adhesive material applied at least to the base of the pad.

28. The device of claim 26, wherein the adhesive means is formed by reacting the prepolymer with ammonium hydroxide during the water actuation thereof.

29. The device of claim 25, wherein the ridge has a longitudinal apex, and wherein the pad is shaped such that a lateral cross-section through the ridge narrows from the base to the apex.

30. The device of claim 29, wherein the pad is shaped such that a lateral cross-section through the ridge has a substantially triangular shape with rounded corners and slightly concave sides.

31. The device of claim 30, wherein the ridge has a tapered anterior edge, whereby the anterior end of the pad is substantially reduced in thickness as compared to the posterior end.

* * * * *